US006663658B1

(12) United States Patent
Kollias et al.

(10) Patent No.: US 6,663,658 B1
(45) Date of Patent: Dec. 16, 2003

(54) PHOTOTHERAPY METHOD FOR TREATMENT OF ACNE

(75) Inventors: Nikiforos Kollias, Skillman, NJ (US); Robert Gillies, Weston, MA (US); Wei Dong Tian, West Roxbury, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/559,139

(22) Filed: Apr. 27, 2000

Related U.S. Application Data
(60) Provisional application No. 60/131,313, filed on Apr. 27, 1999.

(51) Int. Cl.[7] ............................................. A61B 18/18
(52) U.S. Cl. ............................. 607/88; 607/1; 607/89; 606/3; 606/9
(58) Field of Search ...................... 606/9–19, 131, 606/133; 607/88–90

(56) References Cited

U.S. PATENT DOCUMENTS

| | | | |
|---|---|---|---|
| 4,287,554 A |  | 9/1981 | Wolff .......................... 362/218 |
| 4,651,739 A |  | 3/1987 | Oseroff et al. |
| 4,930,504 A | * | 6/1990 | Diamantopoulos et al. . 128/395 |
| 4,945,908 A | * | 8/1990 | Schneider ................... 128/369 |
| 5,226,907 A |  | 7/1993 | Tankovich |
| 5,304,170 A |  | 4/1994 | Green |
| 5,422,093 A |  | 6/1995 | Kennedy et al. |
| 5,423,803 A |  | 6/1995 | Tankovich et al. |
| 5,425,728 A |  | 6/1995 | Tankovich |
| 5,464,436 A | * | 11/1995 | Smith .......................... 607/89 |
| 5,647,866 A |  | 7/1997 | Zaias et al. |
| 5,669,916 A |  | 9/1997 | Anderson |
| 5,713,845 A |  | 2/1998 | Tankovich |
| 5,735,844 A |  | 4/1998 | Anderson et al. |
| 5,752,948 A |  | 5/1998 | Tankovich et al. |
| 5,752,949 A |  | 5/1998 | Tankovich et al. |
| 5,817,089 A | * | 10/1998 | Tankovich et al. .............. 606/9 |
| 5,925,034 A | * | 7/1999 | Buckley et al. ................. 606/7 |

(List continued on next page.)

FOREIGN PATENT DOCUMENTS

| | | | |
|---|---|---|---|
| EP | 0 726 083 A2 | 8/1996 | ............. A61N/5/06 |
| WO | WO 96/14899 | 5/1996 | ............. A61N/5/06 |
| WO | WO 96/41579 | 12/1996 | |
| WO | WO 97/00098 | 1/1997 | |
| WO | WO 98/33444 | 8/1998 | ............ A61B/17/36 |

OTHER PUBLICATIONS

*Konig, et al. "Photodynamic Induced Inactivation of Propionibacterium Acnes Using the Photosensitizer Methylene Blue and Red Light" *Dermatologische Monatsschrift,* vol. 178, pp. 297–300 (1992).

*Dierickx, et al., "Photodynamic Therapy for Nevus Sebaceus with Topical Aminolevulinic Acid" *Arch Dermatol,* vol. 133, pp. 637–640 (1999).

(List continued on next page.)

*Primary Examiner*—Michael Peffley
*Assistant Examiner*—Peter Vrettakos
(74) *Attorney, Agent, or Firm*—Nutter McClennen & Fish LLP

(57) ABSTRACT

The present invention is directed to methods for treating acne. The methods include exposing the subject afflicted with acne to ultraviolet light having a wavelength between about 320 to about 350 nm, such that the acne is treated, e.g., inhibited, diminished, eradicated or prevented. In a preferred embodiment, the wavelength is 335 nm and is emitted by either a nitrogen laser or a third harmonic of a NdYAG laser. Treatments can be administered over a several week period, where the subject is exposed to sequential doses of ultraviolet light to obtain beneficial effects, e.g., a reduction or elimination of the acne, e.g., an eradication or diminishment of the bacteria responsible for acne, e.g., *Propionibacterium acnes.*

17 Claims, 3 Drawing Sheets

U.S. PATENT DOCUMENTS

| | | | | |
|---|---|---|---|---|
| 5,955,490 A | | 9/1999 | Kennedy et al. | |
| 6,036,684 A | * | 3/2000 | Tankovich et al. | 606/9 |
| 6,063,108 A | * | 5/2000 | Salansky et al. | 607/89 |
| 6,165,170 A | * | 12/2000 | Wynne et al. | 606/10 |
| 6,168,590 B1 | * | 1/2001 | Neev | 606/9 |
| 6,183,773 B1 | * | 2/2001 | Anderson | 424/450 |
| 6,283,956 B1 | | 9/2001 | McDaniel | |
| 6,358,272 B1 | * | 3/2002 | Wilden | 606/13 |

OTHER PUBLICATIONS

*Koning, et al., "Photodynamische Aktivitat von Methylenblau" *Akt. Dermatol,* vol. 19, pp. 195–198 (1993).

*Konig, et al. "Photodynamically Inactivation of Propionibacterium Acnes" *SPIE,* vol. 3247 pp. 106–110 (1998).

*Wilkin, "Pathophysiology and Treatment" *Arch Dermatol,* vol. 130 pp. 359–362 (1994).

Von A. Lassus et al. Treatment of acne with selective UV–phototherapy (SUP). An open trial Dermatol Monatsschr (1993) Jun.;169(6):376–9.

Von H. Meffert et al. Phototherapy of acne vulgaris with the UVA irradiation instrument TBG 400.Dermatol Monatsschr (1986);172(2):105–6.

Von H. Meffert et al. Phototherapy of acne vulgaris with the "TuR" UV 10 body section irradiation unit., Dermatol Monatsschr (1986);172(1):9–13.

Von H. Meffert et al., Treatment of acne vulgaris with visible light, Dermatol Monatsschr (1987);173(11):678–9.

Von H. Meffert et al. Therapy of acne with visible light. Decreased irradiation time by using a blue–light high–energy lamp, Dermatol Monatsschr (1990);176(10):597–603.

Konig, et al. "Photodynamic Induced Inactivation of Propionibacterium Acnes Using the Photosensitizer Methylene Blue and Red Light" *Dermatologische Monatsschrift,* vol. 178, pp. 297–300 (1992).

Dierickx, et al. "Photodynamic Therapy for Nevus Sebaceus with Topical Aminolevulinic Acid" *Arch Dermatol,* vol. 133, pp. 637–640 (1999).

Konig, et al. "Photodynamische Aktivitat von Methylenblau" *Akt. Dermatol,* vol. 19, pp. 195–198 (1993).

Konig, et al. "Photodynamically Inactivation of Propionibacterium Acnes" *SPIE,* vol. 3247 pp. 106–110 (1998).

Wilkin, "Pathophysiology and Treatment" *Arch Dermatol,* vol. 130 pp. 359–362 (1994).

International Search Report, Aug. 7, 2000.

"A New Apparatus with High Radiation Energy Between 320–460 nm: Physical Description and Dermatolgical Applications", Maxim F. Mutzhas, et al., The Journal of Investigative dermatology, 76:42–47, 1981.

"Ultraviolet Phototheraphy and Photochemotherapy of Acne Vulgaris", Otto H. Mills, et al., Arch Dermatol, vol. 114, p. 221–223, Feb. 1978.

"Seasonal Variations in the Severity of Acne Vulgaris", Michael Gfesser, et al., International Journal of Dermatology, vol. 35, No. 2, pp. 116–117, Feb. 1996.

"Phototherapy of Acne Vulgaris with Visible Light", V. Sigurdsson, et al., Dermatology, 194, 256–260, 1997.

"Singlet Oxygen ($^1\Delta_g$) Generation from Coproporphyrin in Propionibacterium acnes on Irradiation", Kumi Arakane, et al., Biochemical and Biophysical Research Communications, Article No. 0937, 578–582, 1996.

"Changes in polyphosphate composition and localization in Propionibacterium acnes after near–ultraviolet irradiation", B. Kjeldstad, et al., Can J. Microbiol., vol. 37, pp. 562–567, 1991.

"In vivo and in vitro effects of doxycycline on leucocyte membrane receptors", A Næss, et al., Clin exp Immunol. 62, 310–314, 1985.

"Endogenous Skin Fluorescence Includes Bands that may Serve as Quantitative Markers of Aging and Photoaging", Nikiforos Kollias, et al, The Society for Investigative Dermatology, Inc., vol. III, No. 5, pp. 776–780, 1998.

"Safety Analysis: Relative Risks of Ultraviolet Exposure from Fluorescence Spectroscopy and Colposcopy are Comparable", Carrie K. Brookner, et al., Photochemistry and Photobiology, 65(6): 1020–1023, 1997.

* cited by examiner

PHOTOTHERAPY METHOD FOR TREATMENT OF ACNE

CROSS-REFERENCE TO RELATED APPLICATION

This application claims priority to U.S. Provisional Patent Application No. 60/131,313, filed on Apr. 27, 1999, entitled "Phototherapy Method for Treatment of Acne", the contents of which are incorporated herein by reference.

BACKGROUND OF THE INVENTION

Acne is one of the most frequently presented dermatologic conditions. To date there is no single widely accepted treatment modality although a number of approaches exist. These approaches include topical or systemic antibiotics, benzoyl peroxide gels, oral 13-cis-retinoic acid, or hormones. Acne lesions (comedones) are the result of a complex interaction between hormones (androgens) and bacteria (*Propionibacterium acnes*) in the pilosebaceous unit. Acne results when the opening of the sebaceous glands is occluded, resulting in accumulation of sebum and fatty acids produced by the bacteria through lipase breakdown of lipids. The increase in sebum results in enlargement of the glands which in turn leads to inflammation and eventually to rupture of the glandular envelop. Release of the gland contents into the dermis produces changes in the structural matrix and may result in scarring. While acne is not a life threatening condition, it frequently produces discomfort, and can be disfiguring to a subject due to scarring.

Exposure of the skin to ultraviolet radiation has been reported to result in enlargement of the sebaceous glands. This has been found in photoaging studies in hairless mice. It is also known that sun exposure results in amelioration of acne. The response to sunlight may be either due to photodynamic activity (PDT) of coproporhyrin produced by the bacteria, *Propionibacterium acnes,* or due to an effect of the sunlight to the cell differentiation and proliferation. The PDT effect would lead to destruction of the bacteria which in turn would lead to improvement of acne. In this case, short wavelength visible radiation (405–410 nm) should be equally effective in improving acne. However, there is substantial evidence that both light and antibiotics reduce the fluorescence produced by coproporphyrin, the loss of which is not always related to amelioration of the acne condition.

SUMMARY OF THE INVENTION

The present invention is directed to methods for treating acne. The methods include exposing the subject afflicted with acne to ultraviolet light having a wavelength between about 320 to about 350 nm, such that the acne is treated, e.g., inhibited, diminished, eradicated or prevented. In a preferred embodiment, the wavelength is 335 nm and is emitted by a nitrogen laser, a third harmonic of a NdYAG laser, a tunable OPO laser (Optical Parametric Oscillator), or a properly filtered mercury lamp or continuous wave lamp. Treatments can be administered over a several week period, where the subject is exposed to sequential doses of ultraviolet light to obtain beneficial effects, e.g., a reduction or elimination of the acne, e.g., eradication or diminishment of the bacteria responsible for acne, e.g., *Propionibacterium acnes*.

The present invention is also directed to methods for preventing acne. The methods include exposing the subject afflicted with acne to ultraviolet light having a wavelength between about 320 nm to about 350 nm, such that acne is prevented. In one embodiment, ultraviolet wavelengths useful in the invention are between about 325 nm to about 345 nm, preferably between about 330 to about 340 nm, more preferably between about 332 and about 337 nm, and most preferred at 335 nm.

The present invention is also directed to methods for reducing the amount or size of sebaceous glands in a subject. The methods include exposing the subject to ultraviolet light having a wavelength between about 320 and 350 nm, such that the amount or size of sebaceous glands in the subject are reduced.

The present invention is further directed to methods for treating disease states or conditions which cause or are associated with the generation of excess of sebum in sebaceous glands. The invention is also directed to methods for treating disease states or conditions which cause or are associated with the occlusion of sebaceous glands with accumulation of sebum and fatty acids produced by bacteria through lipase breakdown of lipids. These methods include exposing the subject to ultraviolet light having a wavelength between about 320 and 350 nm, such that the buildup of sebum and/or lipids in the sebaceous glands of the pilosebaceous units of the subject are reduced.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
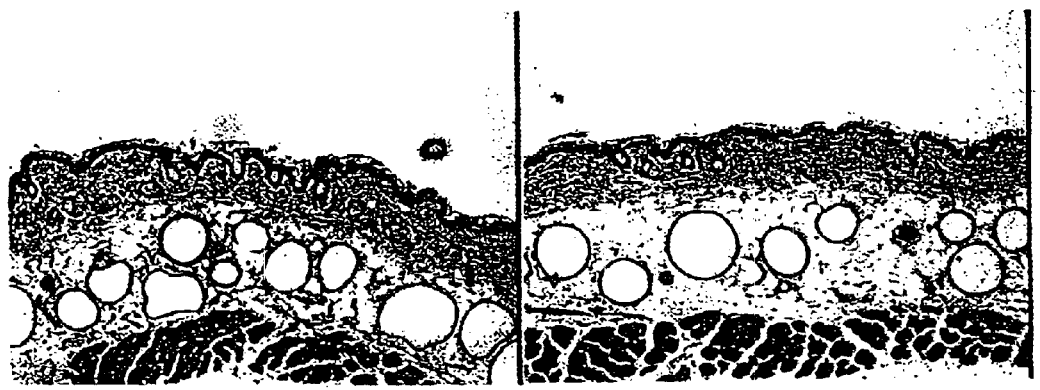
FIG. 1 is a histological section of hairless mouse skin exposed to 335 nm narrow band radiation. Note the absence of sebaceous glands in the exposed site (right), as opposed to the unexposed site (left).

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

In one aspect, the present invention is directed to methods for treating acne. The methods include exposing the subject afflicted with acne to ultraviolet light having a wavelength between about 320 to about 350 nm, such that the acne is treated, e.g., inhibited, diminished, eradicated or prevented. In a preferred embodiment, the wavelength is 335 nm and is emitted by a nitrogen laser, a third harmonic of a NdYAG laser, a tunable OPO laser (Optical Parametric Oscillator), or a properly filtered mercury lamp or continuous wave lamp. Treatments can be administered over a several week period, where the subject is exposed to sequential doses of ultraviolet light to obtain beneficial effects, e.g., a reduction or elimination of the acne, e.g., eradication or diminishment of the bacteria responsible for acne, e.g., *Propionibacterium acnes*.

The terms "treating" or "treatment" are intended to include eradication of, inhibition of, prevention of and/or diminishment of disease states or conditions associated with pore blockage by sebum or lipids produced by the sebaceous glands. In a preferred embodiment, the occurrence of acne, measured by reduction of blackheads, whiteheads and/or the amount of sebaceous glands or size of sebaceous glands in a subject, is diminished, preferably by at least 30%, more preferably by at least 50%, even more preferably by at least 90%, and most preferably by at least 99%. Preferably, the occurrence of acne or a related condition is eliminated from the subject.

The term "subject" is intended to include living organisms susceptible to conditions or diseases caused or contributed to by overstimulation or production of sebum from sebaceous glands. Examples of subjects include humans, dogs, cats, cows, goats, and mice. The term subject is further intended to include transgenic species.

The term "acne" is art recognized and is intended to include acne vulgaris and acne rosacea. The term encompasses the condition(s) associated with the complex interactions between hormones and bacteria in the pilosebaceous unit which often result in comedones. Acne vulgaris is the most common skin disease seen in dermatologic practice which affects millions of people in the United States. Abnormal keratin production with obstruction of the follicular opening, increased production of sebum (lipids secreted by the androgen-sensitive sebaceous glands), proliferation of *Propionibacterium acnes* (anerobic follicular diphtheroids), follicular rupture and follicular mites (demodex) are commonly associated with acne.

In acne vulgaris, rupture of a follicle is the event which stimulates inflammation to form a "pimple," including accumulation of pus to form a "whitehead." "Blackheads" (an open comedo) consist of a plugged sebaceous follicle which contains melanin or melanin-oxidized substances which absorb light.

There is no doubt that acne is related to the presence of hyperactive sebaceous glands, no matter what the cause. Therefore, a method which results in diminution of sebaceous gland activity, might be a first necessary step in the development of successful treatment for acne. The present invention is directed to diminishing sebaceous gland activity and/or reduction or destruction of the sebaceous gland.

In another aspect, the present invention is also directed to methods for preventing acne. The methods include exposing the subject afflicted with acne to ultraviolet light having a wavelength between about 320 nm to about 350 nm, such that acne is prevented. Therefore, the methods of the invention can be used prophylactically to reduce or eliminate the possibility of having follicle openings plugged with sebum, dirt and/or lipids.

In one embodiment, ultraviolet wavelengths useful in the invention are between about 320 nm to about 360 nm, between about 325 nm to about 345 nm, preferably between about 330 to about 340 nm, more preferably between about 332 and about 337 nm, and most preferred at 335 nm.

In yet another aspect, the present invention is also directed to methods for reducing the amount or size of sebaceous glands in a subject. The methods include exposing the subject to ultraviolet light having a wavelength between about 320 and 350 nm, such that the amount or size of sebaceous glands in the subject are reduced. The reduction of sebaceous glands in either size or number can be transitory, lasting several days to several weeks, or, more preferably, can be permanent.

The term "sebaceous gland" is art recognized and is a component of the pilosebaceous unit. Sebaceous glands are located throughout the body, especially on the face and upper trunk, and produce sebum, a lipid-rich secretion that coats the hair and the epidermal surface. Sebaceous glands are involved in the pathogenesis of several diseases, the most frequent one being acne vulgaris. Acne is a multi factorial disease characterized by the occlusion of follicles by plugs made out of abnormally shed keratinocytes of the infundibulum (upper portion of the hair follicle) in the setting of excess sebum production by hyperactive sebaceous glands. An advantage of the present invention is that the treatment can permanently alter the sebaceous gland, e.g., eliminate or reduce the number or size or sebaceous glands, rendering the sebaceous gland no longer susceptible to pore pluggage without the side effects of topical or oral drugs.

In still another aspect, the present invention is further directed to methods for treating disease states or conditions which cause or are associated with the generation of excess of sebum in sebaceous glands. The invention is also directed to methods for treating disease states or conditions which cause or are associated with the occlusion of sebaceous glands with accumulation of sebum and fatty acids produced by bacteria through lipase breakdown of lipids. These methods include exposing the subject to ultraviolet light having a wavelength between about 320 and 360 nm, such that the buildup of sebum and/or lipids in the sebaceous glands of the pilosebaceous units of the subject are reduced.

The phrase "disease state or condition" is intended to include those sebaceous gland disorders which can be treated by a narrow range of ultraviolet light, e.g., between about 320 and 360, between about 320 and about 350 nm, preferably between about 325 nm and about 345 nm, more preferably between about 330 nm and about 340 nm, even more preferably between about 332 nm and about 337 nm, and most preferably about 335 nm. Examples of disease states or conditions which can be treated by the methods of the invention include sebaceous gland hyperplasia, acne vulgaris and acne rosacea. Of particular importance is the treatment of acne by the methods of the invention.

Typically the treatment of the subject with ultraviolet light at the preferred wavelengths of the invention is conducted such that the ultraviolet light has a fluence of between about 1 J/cm$^2$ and about 5 J/cm$^2$, preferably about 5 J/cm$^2$. In one embodiment, the treatment is performed between about 0.1 and about 0.5 of the minimum erythema dosage level. Typical fluence rates, for lasers, are between about 5 and 25 millijoules/pulse, more preferably between about 7 and 20 millijoules/pulse, even more preferably between about 10 and 15 millijoules/pulse, and most preferably about 10 millijoules per pulse at about a 10 nanosecond duration, thereby producing approximately between about 2 and about 2 megawatts. Typical fluence rates in non-laser applications are between about 2 and 50 milliwatts/cm$^2$.

In general the methods of the invention are performed over a period of time, usually several weeks, where a treatment is undertaken on a daily, every second or third day, or weekly basis. Ideally, a subject would undergo treatments 3 to 4 times a week for 3 to 4 weeks, with a individual exposures of about 5 J/cm$^2$ of the preferred ultraviolet wavelengths of the invention.

One skilled in the art would be able to choose an energy source which would produce a narrow ultraviolet wavelength between about 320 and about 350 nm, between about 325 and about 345 nm, between about 330 and about 340 nm, between about 332 and about 337 nm and specifically 335 nm. Such energy sources include fluorescent lamps with an internal fluorescent coating that emits only in these particular wavelengths, nitrogen lasers, the third harmonic of NdYAG lasers, or a dye laser whose output is scanned over the area of the skin which requires treatment. The device can be in the shape of a flat panel for chest or back exposure, or it can have the shape of a semicircle for exposing the face.

Sunlight is composed of a broad spectrum of energy wavelengths, including ultraviolet light referred to as UVA and UVB. Although it is generally believed that sunlight generally ameliorates acne, several studies have actually shown that sunlight can increase the occurrence of acne or aggravate the condition. Gfesser and Worret (*Int. J. Derm.* 35, 116 (1996)) studied the effects of sun light and seasonal changes on acne. They concluded that exposure to sun light may have beneficial psychological effects but did not find that sunlight, in general, eliminated acne and, in certain individuals, increased outbreaks of acne. Similarly, Mills et al. (*Brit. J. Derm.* 98, 145 (1978)) found that treatment of individuals with ultraviolet light between 280 and 320 nm actually caused acne to worsen and increased the creation of comedones. Sigurdsson et al. (*Dermatology* 194, 256 (1997)) studied the effects of "full spectrum" light treatment on acne vulgaris above 360 nm and concluded that visible light was a moderately effective treatment for acne. Therefore, it was surprising to unexpectedly find that a narrow band of ultraviolet light would have beneficial effects on the treatment of skin disorders such as acne.

It has been unexpectedly discovered that certain wavelengths of ultraviolet light, e.g., between about 320 to about 350 nm, are capable of producing biological effects in a wavelength specific way. The changes are produced in a fashion similar to selective photothermolysis, i.e., there appears to be a target organelle or appendix within the skin for each wavelength. In particular, it was discovered that multiple exposures to 335 nm light result in significant decrease in the frequency of appearance of sebaceous glands, e.g., in the skin of hairless mice. These wavelength specific biological changes can vary depending on whether continuous light (cw) or a pulsed laser is used.

Figure 2:
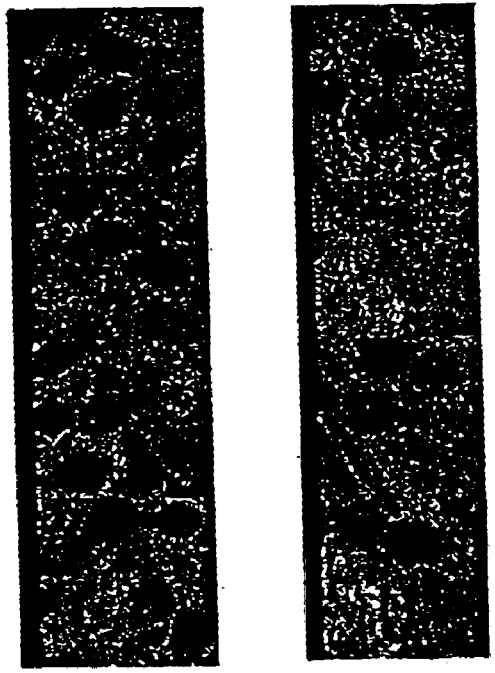
FIG. 2 includes images of the superficial dermis of hairless mouse skin obtained in vivo with an infrared (1.06 $\mu$m) Laser Scanning Confocal Microscope. Four control images corresponding to adjacent skin sites of unexposed hairless mouse skin at a depth of approximately 100 $\mu$m, with the sebaceous glands appearing at this depth as large ellipsoidal bodies (left panel), and four adjacent skin sites that received nine (9) exposures of 335 nm narrow band radiation at 7 J/cm$^2$ per exposure which corresponds to 0.25 of a minimum erythema dose (MED) at this wavelength (right panel). (Unstained sections, 30×magnification, 0.9 NA in water, 250×250$\mu$ field of view).

The present invention is directed to accomplishing these goals by manipulating radiation at the wavelengths where fluorophores present in skin absorb. Selection of the appropriate energy, e.g., ultraviolet wavelength, produces a biological response, in addition to producing changes in the native fluorescence of the skin. In particular, exposure of hairless mice skin to multiple suberythemogenic doses of 335 nm (±10 nm) produces significant reduction in the frequency of appearance of sebaceous glands as well as subtle changes in the collagen matrix. The reduction of the sebaceous gland density has been confirmed with routine histology as well as in vivo by laser scanning confocal microscopy (FIGS. 1 and 2).

Figure 3:
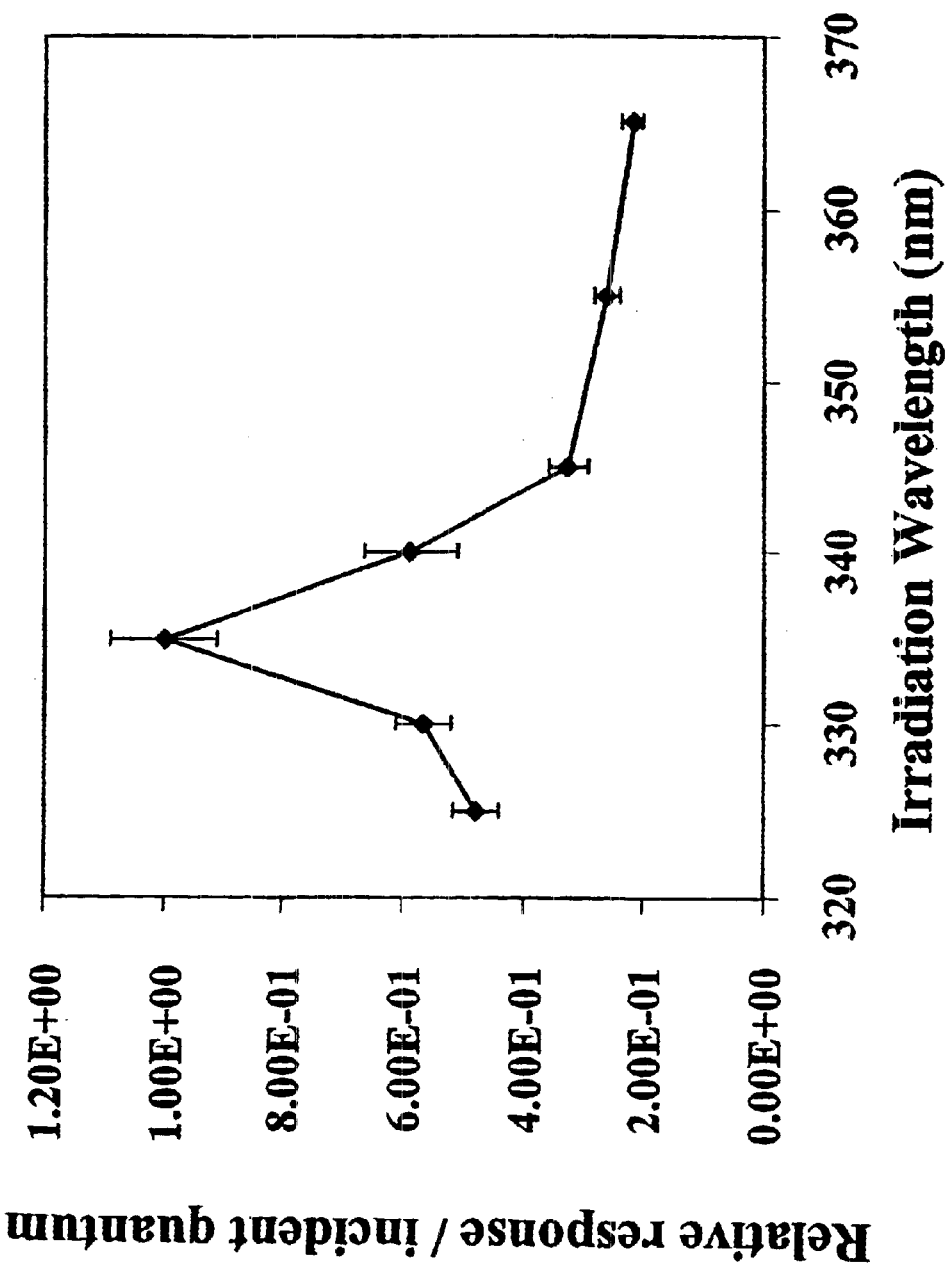
FIG. 3 is an action spectrum for changes in the native fluorescence of skin excited at 335 nm. This fluorescence has been found to be associated with pepsin digestible collagen cross links. The results presented are from hairless mouse skin (n=8) and each animal was exposed (single exposure) on different skin sites on its back at 7 J/cm$^2$ for each wavelength. Illumination was provided by a tunable OPO laser (Optical Parametric Oscillator).

Previous studies have shown that 335 nm radiation is effective in reducing the native fluorescence of hairless mouse skin as well as the fluorescence of human skin. The fluence necessary to produce a twofold decrease is of the order of 1 J/cm$^2$. Unexpectedly, it was discussed that treatment of skin with exposure to ultraviolet light between the range of about 320 nm to about 350 nm, preferably between about 325 nm to about 345 nm, most preferably at 335 nm, reduced sebaceous gland activity and rendered and/or destroyed the sebaceous unit. For example, assuming a typical solar UVA radiation fluence rate of 4 mW/cm$^2$ (summer, no direct sun exposure), there is approximately 1 J/cm$^2$ of solar UVA corresponding to a 5 minute exposure. Changes in fluorescence are produced in a wavelength specific way i.e., the changes produced at 335 nm are produced with 5 times smaller dose than those at 360 nm (FIG. 3).

The mechanism of action for the depletion of sebaceous glands is not well understood because there is not a well characterized absorber in the pilosebaceous unit that absorbs light in this wavelength range. It is considered that a reduction in the number or size of sebaceous units in the hairless mouse would correspond to a similar response in the case of human skin. One consideration is that human skin is thicker with sebaceous glands located further in, which means that they would receive a reduced fluence rate, assuming that the same chromophores are present in both species. However, results on hairless mice indicate the applicability to human skin and the treatment of acne.

Both a continuous wave source as well as an optical parametric oscillator (OPO laser) have been utilized to treat skin. The skin response to the two light sources using similar fluences and fluence rates were different. The laser source (with 10 ns pulses) produced a greater level of inflammatory infiltrate without a clinical erythema response. It is considered that the laser is as effective in reducing the frequency of appearance of sebaceous glands at substantially reduced fluences.

The experiments presented below investigate the details of the interaction of 335 nm radiation on the sebaceous glands of the hairless mouse demonstrate a precise dose response for the laser versus the cw narrow band source, and show the effect of 335 nm radiation on human skin in vivo.

Experimental Methods

1. Dose Dependent Animal Studies

The dose dependence of the reduction in sebaceous glands was tested on 12 mice (rhino mouse model). Sites on the back of each animal were tattooed and then received daily exposures at 0.05, 0.1, 0.2, 0.4, 0.8 MED of 335 nm radiation. The animals were exposed on one side of their back to cw radiation and on the other side with short pulse laser radiation (10 ns). The animals were followed up daily by confocal microscopy in vivo and biopsies were taken at time points after changes in the number of sebaceous glands were documented by confocal microscopy. Exposures were continued for up to 4 weeks on the sites that experienced no adverse effects (erythema, edema, scaling). Biopsies were taken from selected sites at the end of one month of exposures and the rest of the animals were followed up weekly at first and biweekly thereafter for up to 2 months to determine the rate of recovery. Frozen sections were obtained from the biopsied sites for autofluorescence microscopy analysis.

2. Dose Dependence Human Studies

Skin sites (2.5 cm in diameter) of the upper back of 12 normal human volunteers with mild to moderate acne will be exposed to 0.1, 0.25 and 0.5 of an MED (minimum erythema dose) of 335 nm radiation, three times a week. The MED will be first determined for each volunteer. Confocal microscopy images will be obtained from control and exposed sites on a weekly basis. At the end of the treatment period 3 nm biopsies will be taken from treated and control sites. Histological staining will include H&E as well as colloidal iron for evaluating changes induced to the structural matrix. The exposed sites will be followed up for up to 2 months to evaluate recovery of the sebaceous glands.

3. Chromophore Identification

Skin from hairless mice and from humans will be obtained for fluorescence microscopy. Frozen and fresh sections will be prepared and fluorescence spectroscopy will be performed on the frozen and the fresh sections to identify the regions of the dermis where the 335 nm fluorescence originates from. High power pulsed laser radiation at 335 nm will then be used to determine whether the tissue site that absorbs at 335 nm, in order to produce fluorescence is also altered by the laser pulse or whether there are other organelles that are susceptible as well.

One of ordinary skill in the art will appreciate further features and advantages of the invention based on the above-described embodiments. Accordingly, the invention is not to be limited by what has been particularly shown and described, except as indicated by the appended claims. All publications and references cited herein, including those in the background, are expressly incorporated herein by reference in their entirety.

What is claimed is:

1. A method for treating acne, comprising
    exposing a region of skin of a subject afflicted with acne to ultraviolet light having wavelengths substantially contained in a spectral band between about 320 to about 360 nm, and a fluence of between about 1 $J/cm^2$ and about 5 $J/cm^2$, so as to produce a biological response in a target within a layer of the region of skin that effectively enhances treatment of the acne without substantially damaging tissue surrounding the target while limiting overall dose of irradiation.

2. The method of claim 1, wherein said wavelengths are between about 325 to about 345 nm.

3. The method of claim 1, wherein said wavelengths are between about 330 to about 340 nm.

4. The method of claim 1, wherein said wavelengths are between 332 and 337 nm.

5. The method of claim 1, wherein said wavelengths are about 335 nm.

6. The method of claim 1, wherein said ultraviolet light is produced by a nitrogen laser.

7. The method of claim 1, wherein said ultraviolet light is produced by a third harmonic of a NdYAG laser.

8. The method of claim 1, wherein said treatment is performed at between about 0.1 to about 0.5 minimum erythema dose.

9. The method of claim 1, wherein said treatment is conducted over multiple exposure periods.

10. The method of claim 1, wherein said treatment comprises prevention of acne.

11. The method of claim 10, wherein said wavelength is between about 330 to about 340 nm.

12. The method of claim 11, wherein said wavelength is between 332 and 337 nm.

13. The method of claim 12, wherein said wavelength is about 335 nm.

14. The method of claim 1, wherein said treatment is effected to reduce size or amount of sebaceous glands in exposed skin.

15. The method of claim 14, wherein said treatment is performed at between about 0.1 to about 0.5 minimum erythema dose.

16. The method of claim 14, wherein said treatment is conducted over multiple exposure periods.

17. A method for treating acne, comprising
    exposing a region of skin of a subject afflicted with acne to ultraviolet light having wavelengths substantially contained in a spectral band between about 320 to about 360 nm, and a fluence of between about 1 $J/cm^2$ and about 5 $J/cm^2$, so as to produce a biological response in a sebaceous gland within the region of skin that effectively enhances treatment of the acne without substantially damaging tissue surrounding the sebaceous gland while limiting overall dose of irradiation.

* * * * *